(12) United States Patent
Cooper et al.

(10) Patent No.: US 7,361,176 B2
(45) Date of Patent: Apr. 22, 2008

(54) EXTERNAL BONE/JOINT FIXATION DEVICE

(75) Inventors: Paul Cooper, Washington, DC (US);
Mamdouh Elsakka, Warsaw, IN (US);
Joel Mohrman, Fort Wayne, IN (US);
John Pepper, Cheshire, CT (US)

(73) Assignee: DePuy Products, Inc., Warsaw, IN (US)

( * ) Notice: Subject to any disclaimer, the term of this patent is extended or adjusted under 35 U.S.C. 154(b) by 147 days.

(21) Appl. No.: 10/750,416

(22) Filed: Dec. 31, 2003

(65) Prior Publication Data

US 2005/0149018 A1    Jul. 7, 2005

(51) Int. Cl.
*A61B 17/56* (2006.01)

(52) U.S. Cl. ...................................................... 606/54

(58) Field of Classification Search ............ 606/54–55, 606/231, 233, 56–59; 600/231–233
See application file for complete search history.

(56) References Cited

U.S. PATENT DOCUMENTS

| | | | |
|---|---|---|---|
| 2,035,952 A | | 3/1936 | Ettinger |
| 2,204,266 A | * | 6/1940 | Wilcox ........................ 602/39 |
| 2,393,831 A | | 1/1946 | Stader |
| 2,406,987 A | | 9/1946 | Anderson |
| 3,941,123 A | | 3/1976 | Volkov et al. |
| 4,006,740 A | | 2/1977 | Volkov et al. |
| 4,338,927 A | | 7/1982 | Volkov et al. |
| 4,365,624 A | | 12/1982 | Jaquet |
| 4,604,996 A | * | 8/1986 | Nunamaker et al. .......... 606/54 |
| 4,978,347 A | * | 12/1990 | Ilizarov ........................ 606/54 |
| 5,037,425 A | * | 8/1991 | Brown ......................... 606/92 |
| 5,067,954 A | * | 11/1991 | Ilizarov ........................ 606/58 |
| 5,496,319 A | * | 3/1996 | Allard et al. .................. 606/56 |
| 5,776,132 A | * | 7/1998 | Blyakher ...................... 606/56 |
| 5,885,282 A | * | 3/1999 | Szabo .......................... 606/56 |
| 5,931,837 A | * | 8/1999 | Marsh et al. ................. 606/55 |
| 5,997,537 A | * | 12/1999 | Walulik ........................ 606/56 |
| 6,129,727 A | * | 10/2000 | Austin et al. ................. 606/56 |
| 6,162,224 A | * | 12/2000 | Huebner ....................... 606/59 |
| 6,328,737 B1 | * | 12/2001 | Moorcroft et al. ............ 606/57 |
| 6,565,563 B1 | * | 5/2003 | Agee et al. ................... 606/55 |
| 6,964,663 B2 | * | 11/2005 | Grant et al. .................. 606/54 |

* cited by examiner

*Primary Examiner*—Eduardo C. Robert
*Assistant Examiner*—Mary Hoffman
(74) *Attorney, Agent, or Firm*—Maginot, Moore & Beck

(57) ABSTRACT

An external foot/ankle fixation device has a one-piece frame component and a positionable cross bar that allows the attachment of generally anterior/posterior directed fixation wires or rods emanating from the foot/ankle of a patient. The external fixation device provides a stable fixation platform both in-plane and out-of-plane of the object of fixation (e.g. foot or ankle). The fixation device through the cross bar also provides various degrees of angulation of anterior/posterior directed wires in two planes. Posterior angulation components may be provided to the posterior portion of the frame component that provide additional fixation wire/rod angulation variations. Compression rails may also be provided. An optional elevator component may be attached to the bottom of the frame component that does not obstruct access to the soft tissues on the bottom of the foot. The elevator component protects the bottom of the foot from contaminated surfaces.

37 Claims, 12 Drawing Sheets

EXTERNAL BONE/JOINT FIXATION DEVICE

FIELD OF THE INVENTION

The present invention relates to external orthopedic fixation devices and, more particularly, pertains to an external orthopedic bone and/or joint fixation component, such as for the foot and/or ankle.

BACKGROUND OF THE INVENTION

In the orthopedic reconstruction of a patient's bone and/or joint, particularly with respect to bone repair thereof, it is necessary to keep the repaired bone and/or joint in an immobilized and stable state during the healing process. This is accomplished by using a frame construct that typically includes many different fixation components. The various fixation components are utilized to build a fixation device for immobilizing the bone and/or joint. One such fixation component may be an immobilization platform or platform construct.

In the area of the foot and/or ankle, what is known as a foot frame is generally utilized. Current foot frames are typically of an open U-ring type. The open U-rings may comprise a single "horseshoe-shaped" frame or may include myriad pieces that must be assembled during and for use (known as a modular foot frame).

During the particular surgery, one or more wires, pins, or half pins as they are known in the art are implanted through particular bones of the bone/joint (e.g. the foot and/or ankle). These wires, olive wires, pins, or half pins (collectively, wires) are utilized to immobilize and/or apply compression to the particular and/or surrounding bones in order to create a proper healing environment. The wires themselves need to be externally fixed in order to create a desired compression result on the bone or bones and/or joint or joints. This is currently accomplished by tying the wires to wire/rod nuts on the various components of the open U-ring foot frame. These systems, however, suffer problems with respect to being able to achieve the desired compression results, e.g. the ability to adequately externally fix the wires and provide controlled compression. This can lead to instability problems. Moreover, it is difficult to achieve accurate in-plane compression with current fixation devices.

In order to resolve these problems, the prior art bends the transverse wires from the ankle/foot, then tensions the bent wires to achieve compression. This is known as walking the wires. The bent and tensioned wires are then attached to the open U-frame. Tensioning bent wires, however, does not provide a controlled or measurable amount of compression on the desired area of the ankle/foot.

With respect to after surgery and particularly with respect to the foot and/or ankle, the surgical area (ankle/foot area) is exposed. It is thus necessary in some respects to protect the particular area (ankle/foot). Prior art fixation devices utilize an additional ring positioned inferior to the foot frame to protect the bottom of the foot. This technique is time consuming and costly.

In view of the above, there is a need for an external bone and/or joint fixation device that provides improved fixation.

In view of the above, there is a need for an improved external bone and/or fixation device that may be used as part of a larger fixation system.

In view of the above, there is a need for an external foot and/or ankle fixation device that provides improved fixation.

In view of the above, there is a need for an external foot and/or ankle fixation device that provides for greater fixation stability.

In view of the above, there is a need for an external foot and/or ankle fixation device that provides for improved controllable compression.

In view of the above, there is a need for an external foot and/or ankle fixation device that provides accurate in-plane compression.

In view of the above, there is a need for an external foot and/or ankle fixation device that can provide various degrees of fixation member angulation in an anterior/posterior direction.

In view of the above, there is a need for an external foot and/ankle fixation device that includes a dedicated elevator to protect the bottom of the foot from contaminates while still providing access for wound care.

In view of the above, there is a need for an external foot/ankle fixation device that allows adjustable, controlled anterior/posterior compression for medial/lateral fixation members.

SUMMARY OF THE INVENTION

In a general form, the subject invention is an external bone and/or joint fixation device. The fixation device allows the attachment of various anterior/posterior and/or medial/lateral fixation wires or members for immobilizing the bone and/or joint. Such attachment may be made at various angles in the general anterior/posterior direction. Moreover, the fixation device allows controlled compression along various medial/lateral and/or anterior/posterior directions. The fixation device may be used as one construct in a fixation system.

In a specific form, the present invention is an external foot/ankle fixation device. The fixation device has a preferably, but not necessarily, one-piece frame component and a positionable cross bar that allows the attachment of generally anterior/posterior directed fixation wires (e.g. olive wires) or rods emanating from the foot/ankle of a patient. The fixation wires may be attached in various angles relative to an anterior/posterior plane. The external fixation device provides a stable fixation platform both in-plane and out-of-plane of the object of fixation (e.g. foot or ankle).

Through the cross bar, the fixation device also provides various degrees of angulation of anterior/posterior directed fixation wires in two planes. Posterior angulation components may be provided to the posterior portion of the frame component that provides additional fixation wire/rod angulation variations. An optional elevator component may be attached to the bottom of the frame component that does not obstruct access to the soft tissues on the bottom of the foot while still protecting the bottom of the foot from contaminated surfaces.

The ring frame is constructed as a closed, one-piece platform. This provides a stable platform for object fixation. This approach is simple and less expensive than modular alternatives. The present invention solves the instability problems of current open U-ring foot/ankle fixation devices. Additionally, the bottom of the foot of the patient may also be protected. Moreover, the present invention allows the accurate application of in-plane compression using tension or fixation wires. The present invention also allows the capture of fixation wires tied to various degrees of angulation in a posterior/anterior direction.

The present external ankle/foot fixation device is also able to provide controlled and/or incremental compression (to the ankle/foot) for certain wires thereof along the anterior/posterior direction. Distraction and/or initial placement of half pins and the like are also achievable. Preferably movable compression rails are situated on the medial/lateral sides of the foot frame. The compression rails move along the anterior/posterior direction. The compression rails or components provide attachment of medial/lateral fixation wires for anterior/posterior compression.

In one form, there is provided an external bone/joint fixation component. The bone/joint fixation component has a one-piece or modular frame having a posterior portion lying essentially in a first plane and an anterior portion transverse to the posterior portion and lying essentially in a second plane, and a first plurality of fixation bores disposed in the posterior portion and a second plurality of fixation bores disposed in the anterior portion each of which is configured to receive a wire fixator that is adapted to receive an end of a fixation wire.

In another form, there is provided an external bone/joint fixation device. The external bone/joint fixation device includes a frame and a cross bar. The frame component is defined by a posterior portion and an anterior portion disposed transverse to the posterior portion, and includes a plurality of first fixation bores each of which is configured to receive a wire fixator that is adapted to receive an end of a fixation wire. The cross bar component is attachable to the anterior portion of the frame component and has a plurality of second fixation bores each of which is configured to receive a wire fixator that is adapted to receive another end of the fixation wire. The cross bar and the frame component providing controlled compression of a bone or joint retained by fixation wires tied to the frame component and the cross bar.

In yet another form there is provided an external bone/joint fixation device. The bone/joint fixation device includes a frame component and first and second compression rails disposed on the frame component. The frame component is defined by a posterior portion and an anterior transverse portion and includes a plurality of fixation bores.

DETAILED DESCRIPTION OF THE INVENTION

Figure 1:
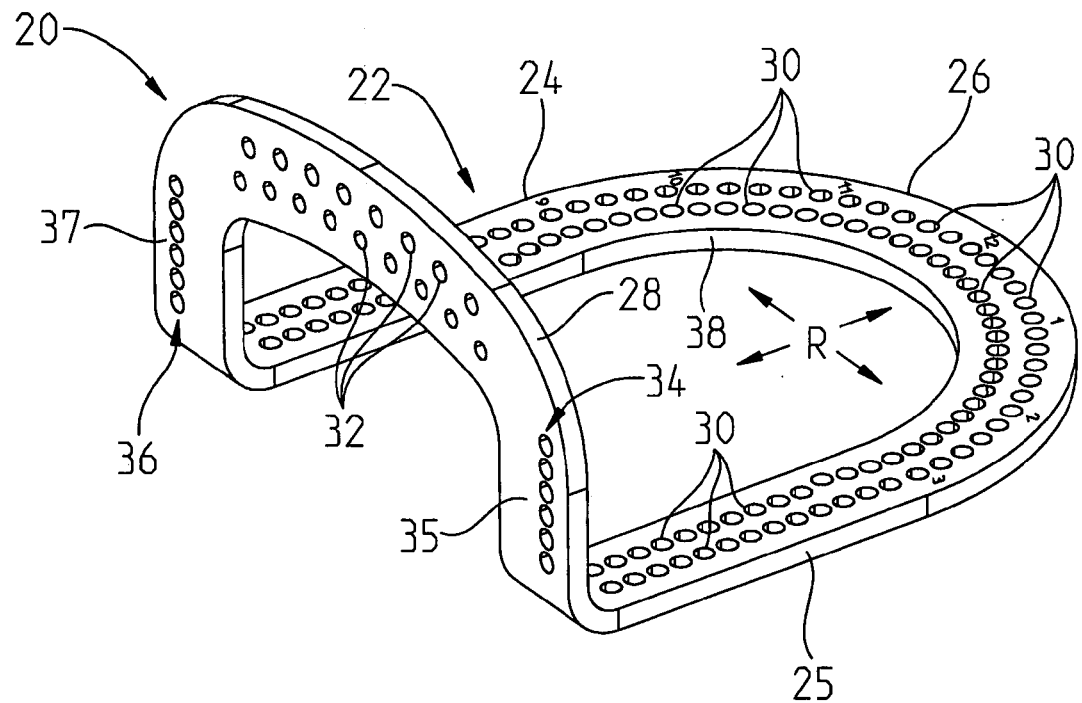
FIG. 1 is a perspective view of a frame component of the present external bone/joint fixation device.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents and alternatives falling within the spirit and scope of the invention as defined by the appended claims.

Referring now to FIG. 1, there is depicted an exemplary embodiment of a frame component (frame), generally designated 20, of a bone/joint fixation device configured in accordance with the principles of the subject invention. While the present bone/joint fixation device or component is shown and described with respect to a foot/ankle device or component, it should be appreciated that the principles and/or the particular embodiments of the present foot/ankle fixation device/component are applicable to bones and/or joints. Moreover, while the present bone/joint fixation device may be utilized as a stand alone device or component, such a bone/joint fixation device is typically utilized in conjunction with other fixation components to create a fixation system.

A body 22 defines the frame component 20 that may take various shapes and be constructed from various angled and non-angled pieces while formed in accordance with the principles presented herein. Thus, while a particular frame shape is shown, it should be appreciated that other frame shapes are contemplated and may fall within the principles of the subject invention. Particularly, the body is defined in first and second planes. The first and second planes are approximately (within an angle), but not necessarily, transverse. The body 22 is configured to surround a bone and/or joint area.

The frame is preferably formed of a unitary piece (i.e. one piece), but may be modular (i.e. more than one piece). The term body (and frame) thus refers to both configurations. The body 22 may be fashioned from a composite material such as carbon fiber, metal, metal alloy, polymer, shape memory polymer, shape memory metals, or other suitable material that provides an adequate stiffness or resistance to torsion, stress, torque and/or other forces that may be applied to the body 22. The material is also preferably, but not necessarily, radiolucent.

The body 22 is generally configured to capture the posterior aspect of a foot and thus may take various shapes. In the embodiment shown, the body 22 is generally formed in the shape of a "U", heel or the like. This may be generally characterized as oblong, oval or ovoid. In the modular case, the body 22 may be formed of variously curved and/or straight pieces. The body 22 has a posterior frame section 26 extending from two side frame sections 24 and 25. The three frame sections 24, 25 and 26 define a geometric plane R. An anterior frame section 28 is disposed at an anterior portion of the frame body 22, particularly extending from other ends of the side frame sections 24 and 25. The anterior frame section 28 is situated in a generally vertical direction relative to the plane R. While not necessary, the anterior frame section 28 is preferably perpendicular to the plane R and thus the posterior frame section 26 and the two side frame sections 24, 25. The anterior frame section 28 may be angled from the perpendicular in both directions.

A plurality of holes, bores, apertures or the like 30 is disposed along the body 22. The holes 30 extend along a posterior portion of the frame body 22 toward the anterior portion (vertical section 28) of the frame body 22. The plurality of holes may be situated anywhere. As such, the plurality of holes 30 may be formed as one or more rows of holes, sets of holes, various pairs of holes (e.g. diametrically opposed pairs of holes), or other configurations or holes. While the holes 30 are depicted in FIG. 1 as formed in essentially two rows extending along the two side portions and the posterior portion of the frame, it should be appreciated that it is not necessary for the holes 30 to be in any particular pattern or formation. It is advantageous to locate the holes 30 in strategic positions with regard to typical foot/ankle fixation members and/or techniques. The holes 30 may be disposed in pre-determined patterns based on typical foot/ankle anatomy. Certain frames may be provided with holes in only particular strategic locations that correspond to typical fixation configurations and/or techniques. A pattern such as that shown, though, allows precise alignment and anchoring of tension wires from and relative to the frame by the physician for foot/ankle fixation. Each bore 30 is adapted, configured and/or operative to receive and retain a twist-on wire connector or the like (not shown in FIG. 1) that is designed to releasably retain a portion (such as an end) of a fixation member such as a tension wire, olive wire or the like.

A first plurality of bores 34 forming a first series or set of bores is disposed on a leg or leg portion 35 of the anterior frame section 28. A second plurality of bores 36 forming a second series or set of bores is disposed on another leg or leg portion 37 of the anterior frame section 28. The first and second set of bores 34, 36 are adapted, configured and/or operative to allow a bolt or other fastening device to extend therethrough. Each set of bores 34 and 36 permits the fastening of a cross bar holder such as the cross-bar holder 40 particularly shown in FIGS. 3 and 4.

Each cross-bar holder 60 is held against a leg 35, 37 of the anterior frame member 28 through a single respective bore 34, 36. While explained in greater detail below, a cross-bar holder 60 may be positioned in and held by any one bore of a respective set of bores 34, 36. Particularly, a cross-bar holder 60 may be positioned in any one bore of the bores of the set of bores 34, while another cross-bar holder 60 may be positioned in any one bore of the set of bores 36. This allows for each cross-bar holder 60 to be in corresponding bore of the two sets of bores 34, 36. This also allows for each cross-bar holder 60 to be in different (non-corresponding) bore of each set of bores 34, 36. When the cross-bar holders are in corresponding bores 34, 36, the cross bar 40 is generally coplanar with the plane R. When the cross-bar holders are in non-corresponding bores 34, 36, the cross bar 40 is at an angle with respect to the plane R (i.e. angulation). This allows tension wires to be situated in various angulations with respect to the plane R (and thus the foot/ankle).

Figure 12:
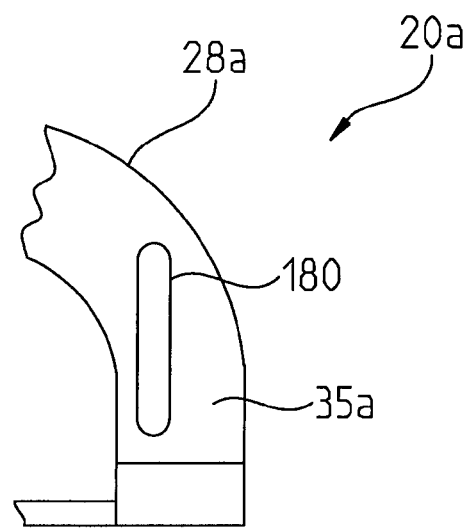
FIG. 12 is an enlarged fragmentary view of one leg of the anterior frame section of the fixation device showing an alternative embodiment to discrete cross bar angulation bores, particularly showing a continuous cross bar angulation slot.

The bores 34, 36 are preferably ovoid or elliptical in shape. This allows a range of adjustment for a bolt received in a bore when the cross-bar holders are situated in non-corresponding bores 34, 36. Moreover, this accommodates the translation of the bolt when the cross bar 40 is in a diagonal state. This result may be achieved by other means. Referring to FIG. 12, there is depicted a leg 35a of an anterior frame section 28a of an exemplary alternative embodiment of an ankle/foot fixation frame 20a. Rather than discrete bores, the leg 35a has a slot or channel 180. This provides continuous cross bar adjustment and diagonal placement accommodation. The slot 180 may be configured in other manners.

The anterior frame section 28 includes a plurality of bores 32 forming a third series or set of bores. Each bore 32 is adapted, configured and/or operative to receive and retain a fixation post or the like (not shown in FIG. 1) that is designed to releasably retain a portion (such as an end) of a tension wire. The body 22 of the frame component 20 may also include demarcation or tensioning marks shown in FIG. 1 as numbers 9-12 and 1-3. These correspond to general clock nomenclature. Other types of calibration marking may be used. The calibration markings may correspond to like markings on other components in order to provide alignment of fixation rods.

The anterior frame section 28 is not necessarily perpendicular to the sides 24, 25. The legs 35 and 37 of the anterior frame section 28 may be angled anywhere from 70°-120° from the perpendicular. Preferably, such an angle is from 80°-110° and is most preferably 90° (perpendicular).

It should be appreciated that the frame component 20 may be made in various sizes, such as small, medium and large, both with respect to the frame itself and particularly to the inner area of the frame (i.e. the area surrounded by or within the frame). This may also be the area between the two legs of the body 22 as depicted in the embodiment of FIG. 1.

The size (area) may range from 130 mm to 220 mm and preferably from 150 mm to 190 mm. The body 22 has an inner arcuate edge 38 that bounds and thus defines an inner area. The inner area is where the foot and/or ankle of a patient is generally retained typically through fixation members that extend into and out of a foot and/or ankle of a patient (not shown) in locations best determined by a physician. By having frame sections (side sections 24, 25, posterior section 26, and anterior section 28) of different dimensions, the frame component 20 may accommodate feet of various dimensions. The frame component 20 may also be made with posterior sections 26 and/or anterior sections 28 of different rates of curvature. Various configurations including modification of the ovoid shape of the frame component 20 may also be made in accordance with an aspect of the principles of the subject invention and is contemplated. Moreover, a set of frames of various dimensions may be provided. The thickness of the frame may range from 0.06 to 0.5 inches and is preferably 0.25 inches.

Figure 2:
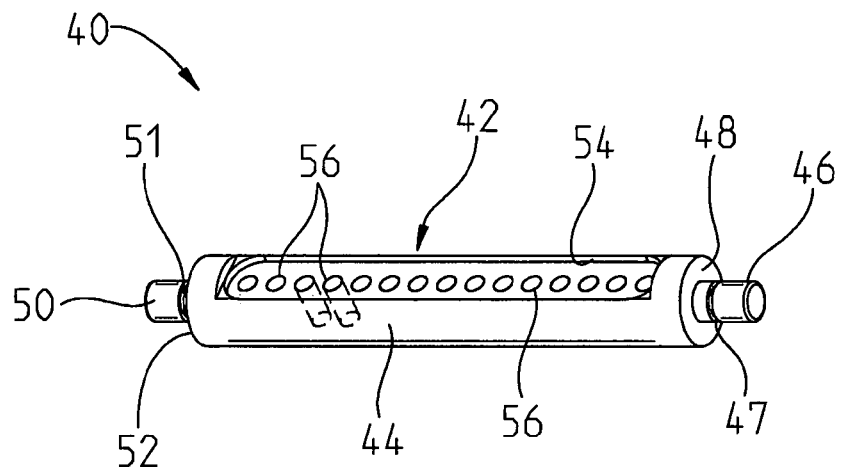
FIG. 2 is a perspective view of a cross-bar component of the present external bone/joint fixation device.

Referring now to FIG. 2, there is depicted an exemplary embodiment of an anterior angulation member generally designated 40 made in accordance with an aspect of the principles of the subject invention. The angulation member 40 is embodied in FIG. 2 as a cross bar. The cross bar 40 is configured to receive and retain fixation posts for retention of tension members such as tension wires. Moreover, the cross bar 40 is adapted to be attached to the frame component 20 as described below. The cross bar 40 is preferably fabricated from a metal, metal alloy, composite, polymer, shape memory polymer, memory shape metal, or similar material that can provide an appropriate stiffness and/or be radiolucent.

The cross bar 40 is defined by a body 42 that, in this embodiment, has a tubular or cylindrical shaped section 44. Of course, other body shapes are contemplated. A neck 46 axially extends from one end 48 of the body section 44. The neck 46 is operative, configured and/or adapted to allow operative attachment of the end 48 (a portion of) the body section 44 to the frame component 20. As well, the neck 46 may be fashioned in other configurations. An O-ring groove 47 is disposed in the surface of the neck 46. A neck 50 extends from another axial end 52 of the body section 44. The neck 50 is operative, configured and/or adapted to allow operative attachment of the end 52 (a portion of) of the body section 44 to the frame component 20. The neck 50 may be fashioned in other configurations. An O-ring groove 51 is disposed in the surface of the neck 50.

The body 42 includes a plurality of bores 56 each one of which preferably, but not necessarily, extend through the body section 44. The openings of each bore 56 is defined in a recess, trough, channel or the like 54 (an opposite recess of which cannot be seen in FIG. 2). The recess 56 is sized to have fixation posts, twist-on wire connectors or the like that are disposed thereon maintain a low profile and/or be below the surface of the recess 56. The cross bar 40 is configured to be immovably, but releasably, fixed in a particular angular orientation and/or in a particular rotational orientation relative to the anterior of the frame component 20.

Figure 3:
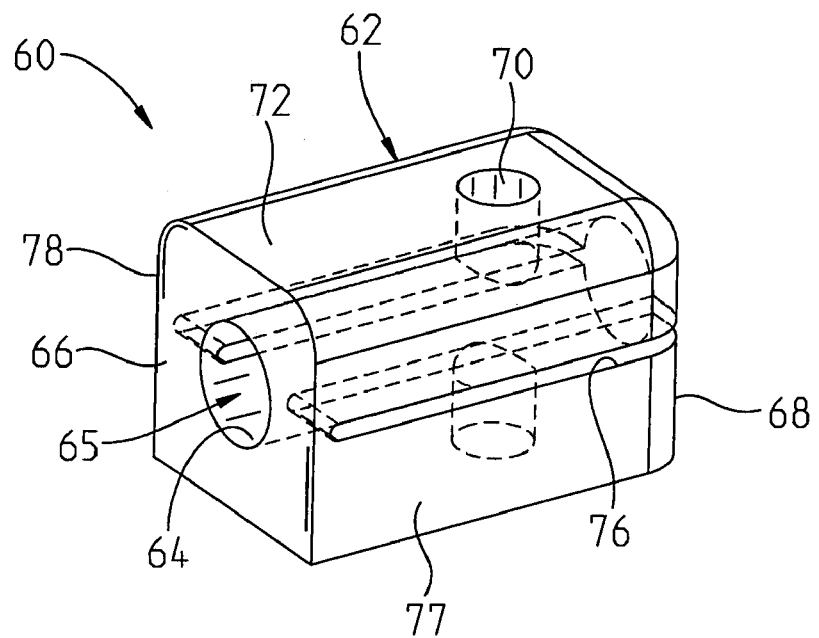
FIG. 3 is an enlarged perspective view of a cross bar holder of the present external bone/joint fixation device.
Figure 4:
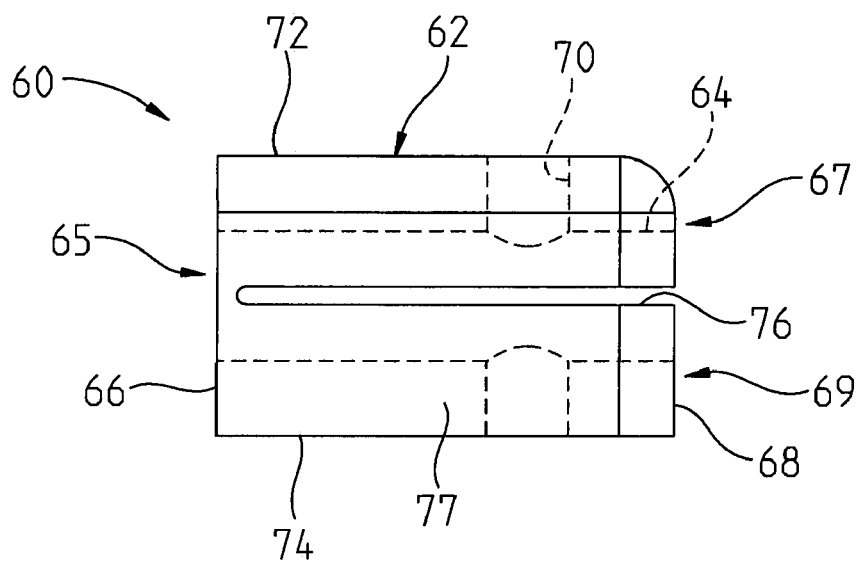
FIG. 4 is an enlarged side view of the cross bar holder of FIG. 3.

Referring now to FIG. 3, there is depicted an enlarged perspective view of an exemplary cross bar holder or clamp generally designated 60. The cross bar holder 60 is utilized to releasably retain one end of the cross bar 40 and to be releasably fastened or mounted to the frame component 20. Because of its clamping function, the cross bar holder 60 also allows the rotational positioning of the cross bar 40 relative to the frame component 20. Two cross bar holders 60 retain the cross bar 40 in a fixed anterior position or angle (angulation) and rotationally orientated relative to the frame component 20.

The cross bar holder 60 is characterized by a body 62 here shown as a generally slightly elongated block. The body 62 has a bore 64 extending from a face 66 of the body 62 to an opposite face 68. The bore 64 defines an opening or shaft 65 that is sized to receive, with preferably little clearance, a neck of the body 42 of the cross bar 40. When the holder 60 is an unclamped state, the opening 65 allows receipt of a neck of the cross bar 40 and the rotation (around a longitudinal axis) of the cross bar 40. When the holder 60 is in a clamped state, the opening 65 is clamped tightly around the neck preventing rotation and extraction.

In order to provide the above-mentioned clamping feature, the body 62 has a longitudinal slot, slit, groove, channel or the like 76 that extends through side face 77 to another side face 78 in one direction, and from the end face 68 to a point in the body 62 a distance from the other end face 66. The slot 76 allows the body 62 to serve as a clamp around a neck of a cross bar 40 that is in the bore 64 when compression is applied to the body 62. This is best understood with reference to the side view of the cross bar holder 60 depicted in FIG. 4. A bolt bore 70 is also disposed in the body 62 extending from the upper surface 72 to the lower surface 74. The bolt bore 70 is proximate the end face 68.

When a bolt or the like is received in the bolt bore 70 and secured with a nut or the like, compression of the body 62 will result. Particularly, compression of a first portion 67 of the body 62, defined as an upper half of the body 62 by the slot 76, and a second portion 69 of the body 62, defined as a lower half of the body 62 by the slot 76, against one another closes the gap size of the slot 76 resulting in a decreased diameter opening 65. The amount of compression determines the reduction of diameter size of the opening 65 and thus the tightness of the clamping.

Figure 5:
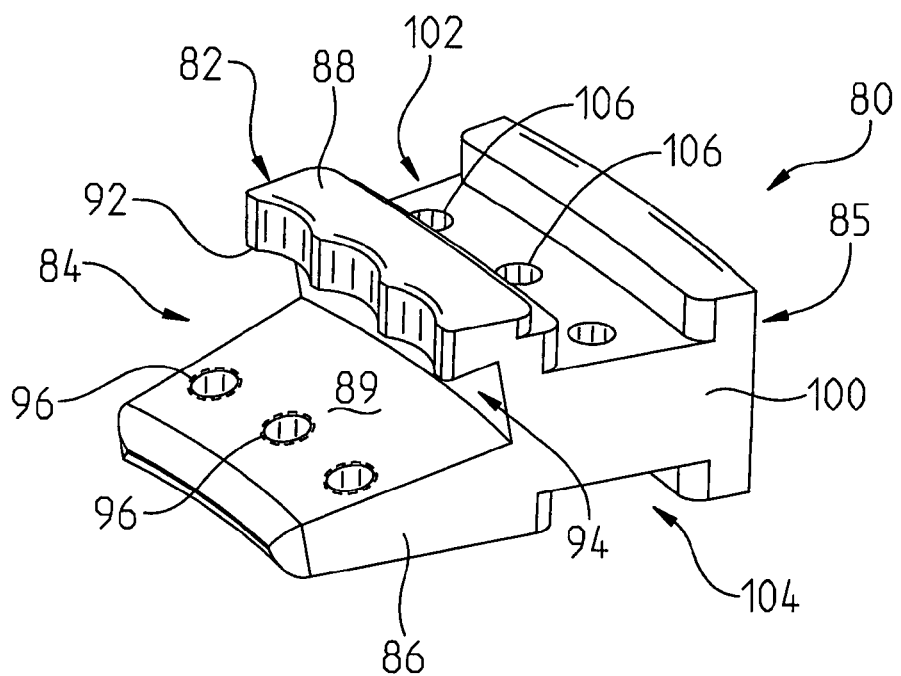
FIG. 5 is an enlarged perspective view of a posterior angulation component of the present external bone/joint fixation device.
Figure 6:
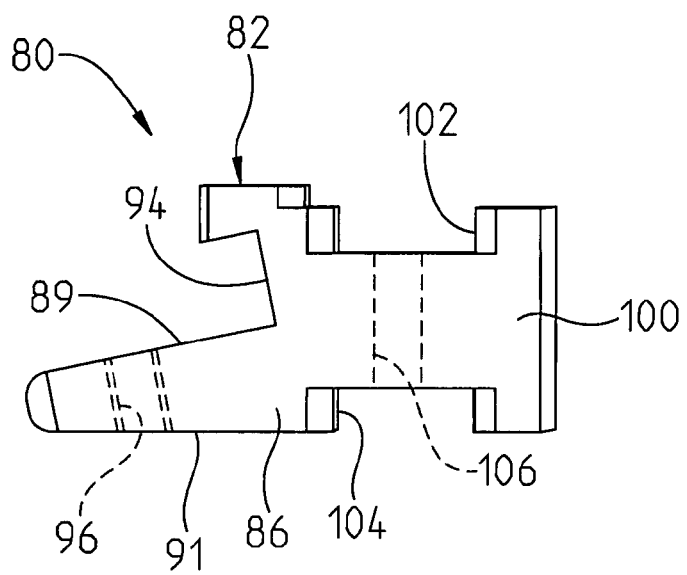
FIG. 6 is an enlarged side view of the posterior angulation component of FIG. 5.

Referring now to FIGS. 5 and 6, there is depicted an exemplary embodiment of a posterior angulation component generally designated 80. The posterior angulation component 80 is adapted, configured and/or operative to allow the retention of fixation wires and/or rods via fixation posts (not seen in FIGS. 5 and 6). The posterior angulation component 80 is further adapted, configured and/or operative to attach to the posterior portion (end 26) of the frame body 22.

Figure 8:
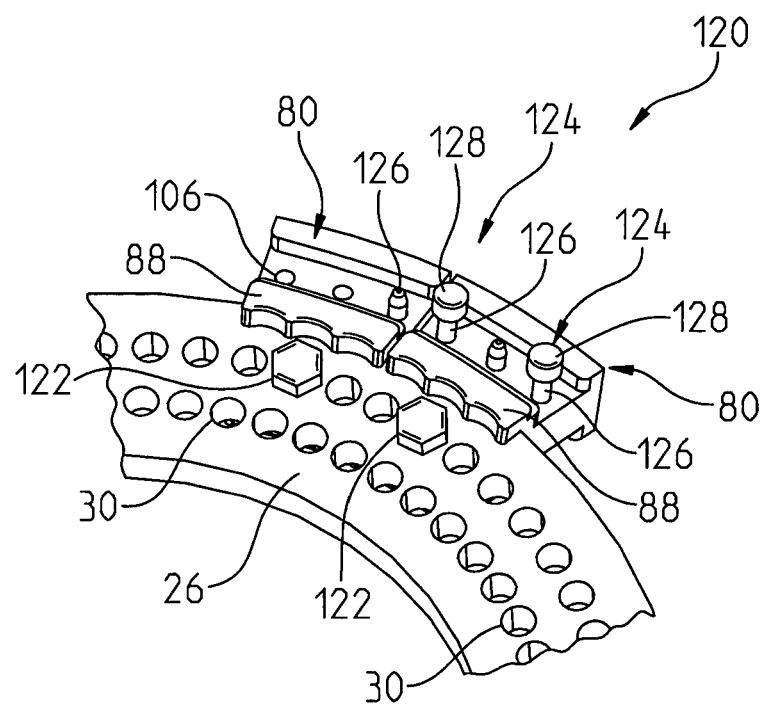
FIG. 8 is a fragmentary view of a portion of the posterior section of the frame component with two posterior angulation components attached thereto.

The posterior angulation component 80 is formed by a body 82 defining a frame attachment portion 84 and a fixation post portion 85. The frame attachment portion 84 is configured, adapted and/or operative to allow the posterior angulation component 80 to be securely attached to the frame 20 and particularly, to an outer portion of the posterior frame section 26 off the body 22 of the frame component 20 such as is shown in FIG. 8.

The frame attachment portion 84 is characterized by a first section 86 having an upper bar 88 extending generally perpendicular from a first surface 89 of the first section 86. The upper bar 88 has an overhanging ledge 92 that along with a portion of the first surface 89 defines a channel 94. The height or thickness of the channel 94 is dimensioned to receive a portion of the frame body 22, particularly at the posterior portion 26 thereof. The channel 94 is also slightly curved in approximately the same curvature as the posterior portion 26 of the frame body 22.

It should be appreciated that the posterior angulation piece 80 may come in different sizes to accommodate different sizes of frames. With respect to the embodiment of FIG. 1, the various posterior pieces would have different radius of curvatures in order to be accommodated on frame sizes having different radii of curvature. One posterior piece, however, may accommodate more than one frame size.

A plurality of holes 96, here depicted as three holes, are disposed in the first section 86 and extend from an upper surface thereof to a lower surface thereof. The holes 96 are configured to allow mounting bolts or the like to extend therethrough in order to allow the attachment of the body 82 to the frame body 22. When installed, each hole 96 may accommodate a mounting bolt.

The fixation post portion 85 of the body 82 includes a lower trough or channel 104 and an upper trough or channel 102 in a rear body portion 100. A plurality of bores 106 are disposed in the rear body portion 100 providing communication between the upper trough 102 and the lower trough 104. The bores 106 are configured to receive a wire or rod fixation post of a wire or rod fixation member (see FIG. 8). The lower trough 104 allows the use of a tool to retain, tighten and/or loosen a nut or other fastening device to a wire/rod fixation post. The upper trough 102 allows access to a wire/rod fixation member knob for retaining a wire and/or rod thereto during use. The upper surface 89 and the lower surface 91 are both angled upward relative to a posterior/anterior direction. This allows the attachment of fixation wires to the posterior angulation device 80 and the cross bar 40. This is best seen in FIG. 10.

Figure 10:
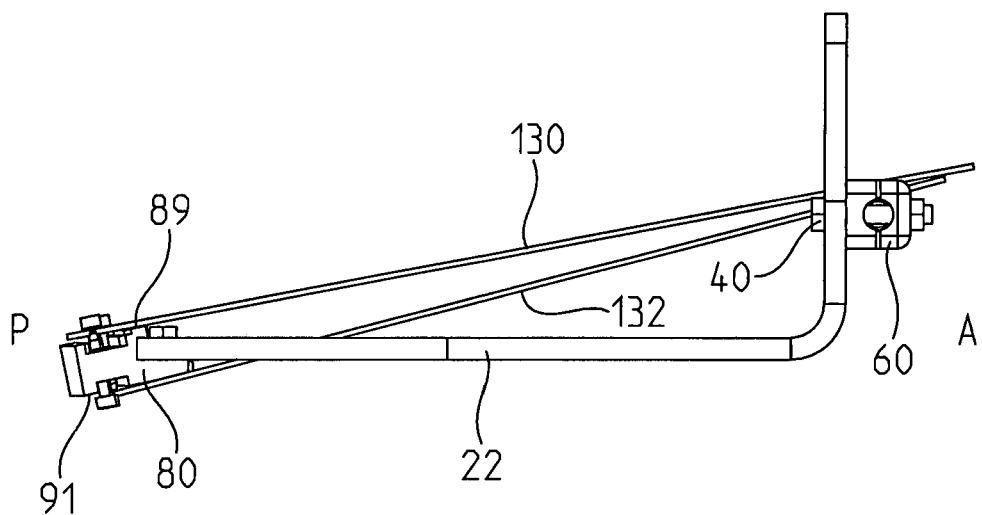
FIG. 10 is a side view of the present fixation device showing exemplary placement of tension rods, wires, half pins or the like without depicting a foot.

As seen in FIG. 10, the upper and lower angled surfaces of the posterior angulation device 80 allows the fixation wires 130 and 132 to extend from the posterior angulation device 80, through the plane of the frame 20, and be coupled to the cross bar 40. The configuration allows the fixation wires to go through the frame.

Figure 7:
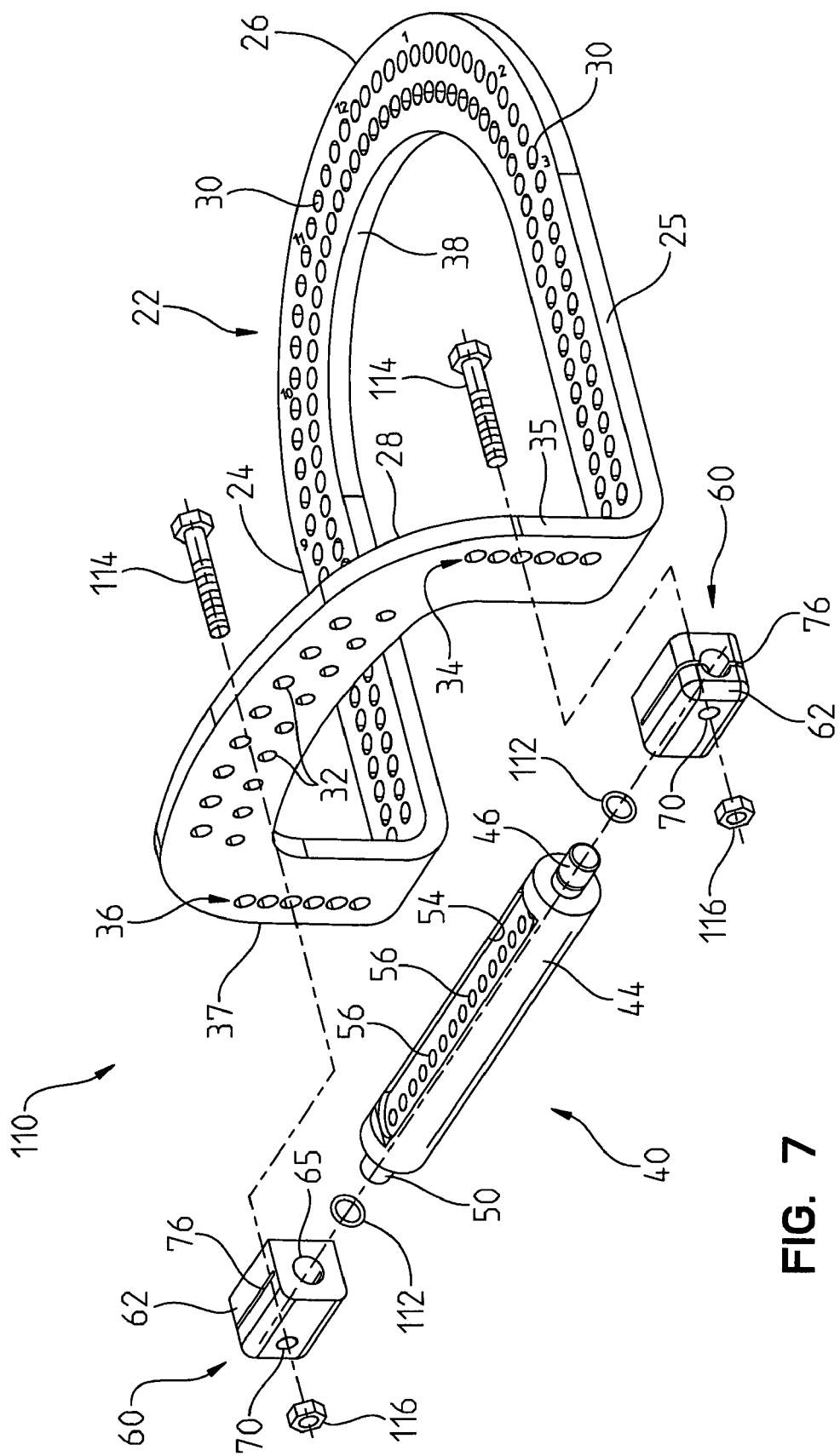
FIG. 7 is an exploded perspective view of one form of the present external bone/joint fixation device.

Referring to FIG. 7, there is depicted an exploded view of an exemplary fixation device generally designated 110. The fixation device 110 is formed by the frame component 22, a cross bar 40, two cross bar holders 60, and a bolt assembly comprising a bolt 114 and nut 116.

Particularly, the opening 65 of a cross bar holder 60 receives a neck 46, 50 of the cross bar 40 after receipt of an o-ring 112 on the neck. One cross bar holder 60 is attached to one bore of the plurality of bores 34 of the leg 35 via a bolt 114 extending through the selected bore 34 and the bolt bore 70 of the particular cross bar holder 60 and secured by a nut 116. The other cross bar holder 60 is attached to one bore of the plurality of bores 36 of the leg 37 via another bolt 114 extending through the selected bore 36 and the bolt bore 70 of the particular cross bar holder 60 and secured by a nut 116. The cross bar 40 provides an anterior positioning/retention device for attachment and retention of one or more fixation or tension wires/rods.

It should be appreciated that each cross bar holder 60 may be positioned in any one of the plurality of holes 34 on one side, and in any one of the plurality of holes 36 on another side. When each cross bar holder is in the same hole position, the cross bar 40 is generally co-planar with the plane R (which generally corresponds to the sole of a foot). The elevation of the cross bar 40 is dependent upon which set of holes 34, 36 the cross bar holders are situated on. FIG. 7 depicts six (6) co-planar positions of the cross bar 40 each at a different elevation relative to the plane R (i.e. six pairs of holes 34, 36). Additionally, and as contemplated, the cross bar 40 may be positioned in various angular orientations relative to the plane R by positioned the cross bar holders in non-paired holes 34, 36. Moreover, the cross bar 40 may be rotated about its longitudinal axis before the cross bar holders 60 are tightened.

Reference is now directed to FIG. 8 where there is depicted a posterior angulation assembly generally designated 120 as part of a fixation device in accordance with an aspect of the principles of the subject invention. Particularly, the posterior angulations assembly 120 depicts two posterior angulation components 80 attached to the posterior portion 26 of the frame body 22. The posterior angulation components 80 are each attached via an attachment bolt 122 that each extend through a respective hole 30 in the posterior portion 26 and a respective hole 96 in the respective front portion 86 of the posterior angulation component 80 (see FIGS. 6 and 7).

One of the posterior angulation components 80 includes two fixators or fixation assemblies 124. Each fixation assembly 124 is configured, adapted and/or operative to releasably retain a fixation wire or rod. The fixation assemblies 124 include a fixation post 126 and a fixation knob 128. A fixation post 126 is shown on the other posterior angulation component 80.

Each posterior angulation component 80 may be positioned anywhere along the posterior portion 26 of the frame 20 and may have up to three fixation assemblies 124 (corresponding to the three holes). A fixation or tension wire or rod is attached to a fixation assembly 124 at the posterior end to provide in-plane anterior to posterior fixation.

Figure 9:
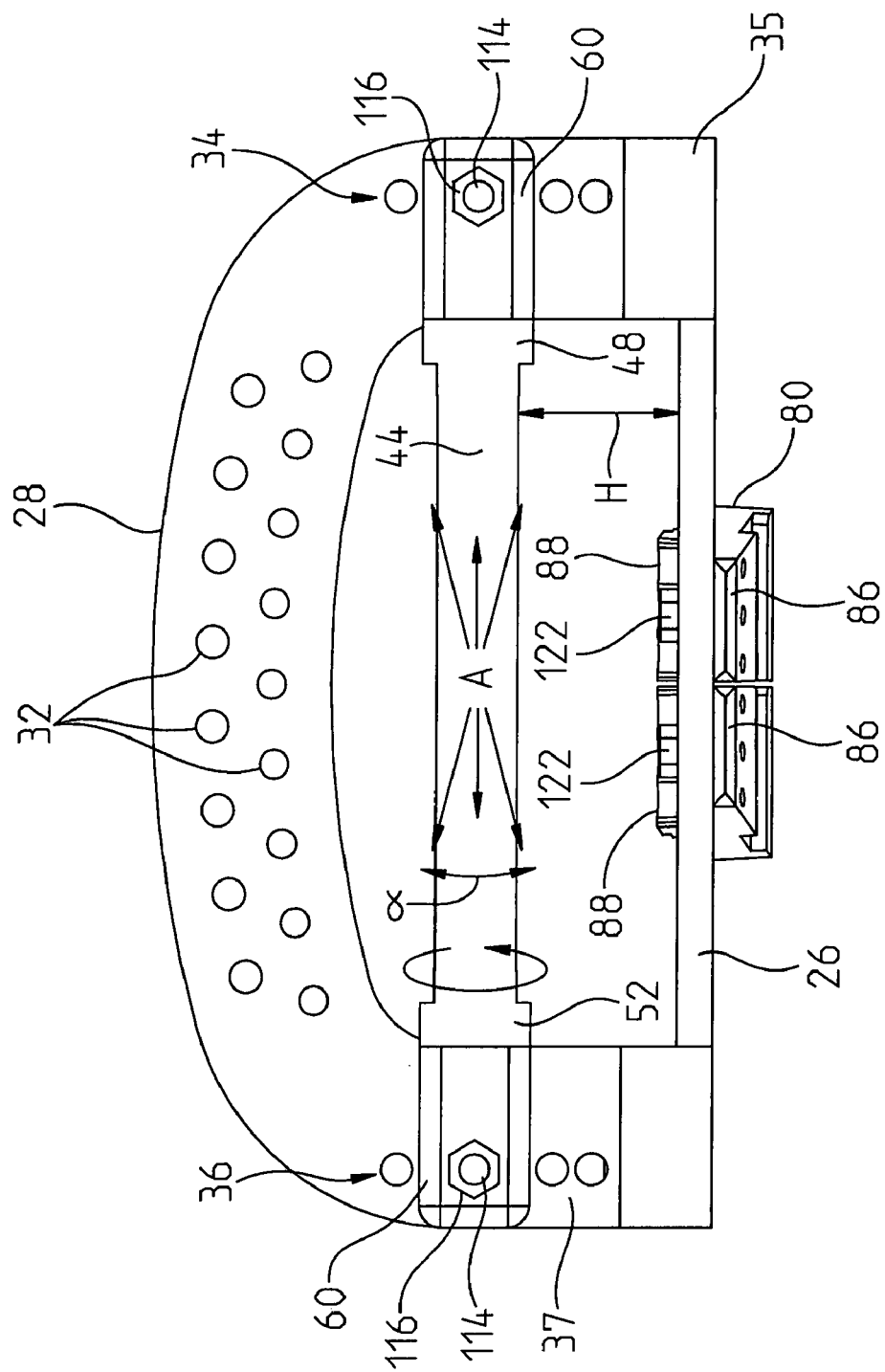
FIG. 9 is an anterior to posterior view of an exemplary configuration of a fixation device in accordance with an aspect of the principles of the subject invention.

FIG. 9 depicts an end (anterior) view of the fixation device having the two posterior angulation components 80 attached to the frame component 20. It should be appreciated that fixation wires may extend from one of the holes 32 via a fixation assembly and extend to either one of the holes 30 in the frame 20 and/or a posterior angulation component 80. Generally, the wires/rods extend in an anterior/posterior (A/P) direction.

FIG. 9 also illustrates the ability of the present fixation device to provide various angulations or angular alignments for the A/P relative to the plane R of the frame component 20. Particularly, the cross bar 40 is able to change its height (H) relative to the plane R (see FIG. 1). This is accomplished by selectively attaching the cross bar holders 60 in appropriate holes 34, 36 of the legs 35, 37. Additionally, the cross bar 40 may rotate as indicated by the arrow. Moreover, the cross bar 40 may assume various angles (A) relative to the plane R. This is accomplished by attaching the cross bar holders 60 to non-paired holes 34, 36. The various positions provide angular variance from a coplanar position of the cross bar 40 with the plane R.

In FIG. 10, there is shown a side view of an external fixation device having a fixation wire or rod 130 extending from the cross bar 40 in a posterior/anterior (P/A) or anterior/posterior (A/P) direction. A foot would be positioned with the heel at the posterior portion (P). Other fixation wires/rods would typically be used. The fixation wire 130 is angled from the upper angled surface 89 of the posterior angulation component 80 and terminates at the cross bar 40.

Another fixation wire 132 is provided from the underside of the posterior angulation component 80. Particularly the fixation wire 132 is angled from the lower angled surface 91 of the posterior angulation component 80. The fixation wire 132 terminates at the cross bar 40.

Figure 11:
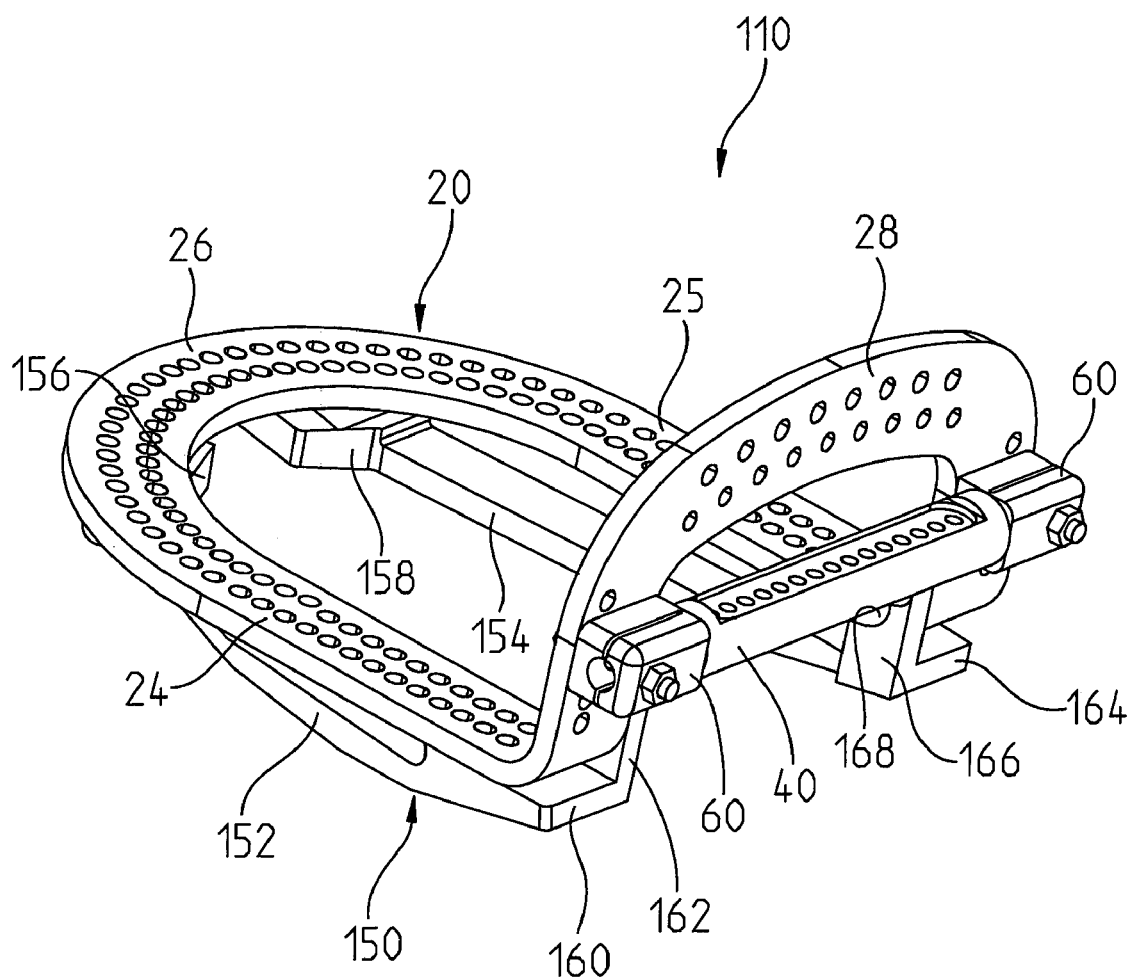
FIG. 11 is a perspective view of an exemplary external bone/joint fixation device having an exemplary foot elevator in accordance with an aspect of the principles of the subject invention.

FIG. 11 depicts an elevator, elevator component, elevator frame component generally designated 150 attached to the bottom of the frame component 20. The elevator 150 is defined by two legs 152 and 154 that correspond to frame portions 24 and 25 and thus run the length thereof. Additionally, the elevator 150 has two front portions 156, 158 that support the posterior portion 26 of the frame component 20. This open concept allows access to the sole of a foot retained therein.

The elevator 150 also has a first pedestal 160 disposed at the anterior end of the leg 152, and a second pedestal 164 disposed at the anterior end of the leg 154. The pedestals 160 and 164 each include a respective stand 162, 166, each of which has an angulation notch (of which only notch 168 is easily discernable). This allows a change in elevation of the elevator 150 relative to the frame component 20.

The elevator 150 is adapted, configured and/or operative to withstand some pressure applied thereto, especially the bottom thereof. Moreover, the elevator 150 is designed to distribute applied pressure evenly thereabout. This alleviates a pressure point when applied to the frame.

Figure 13:
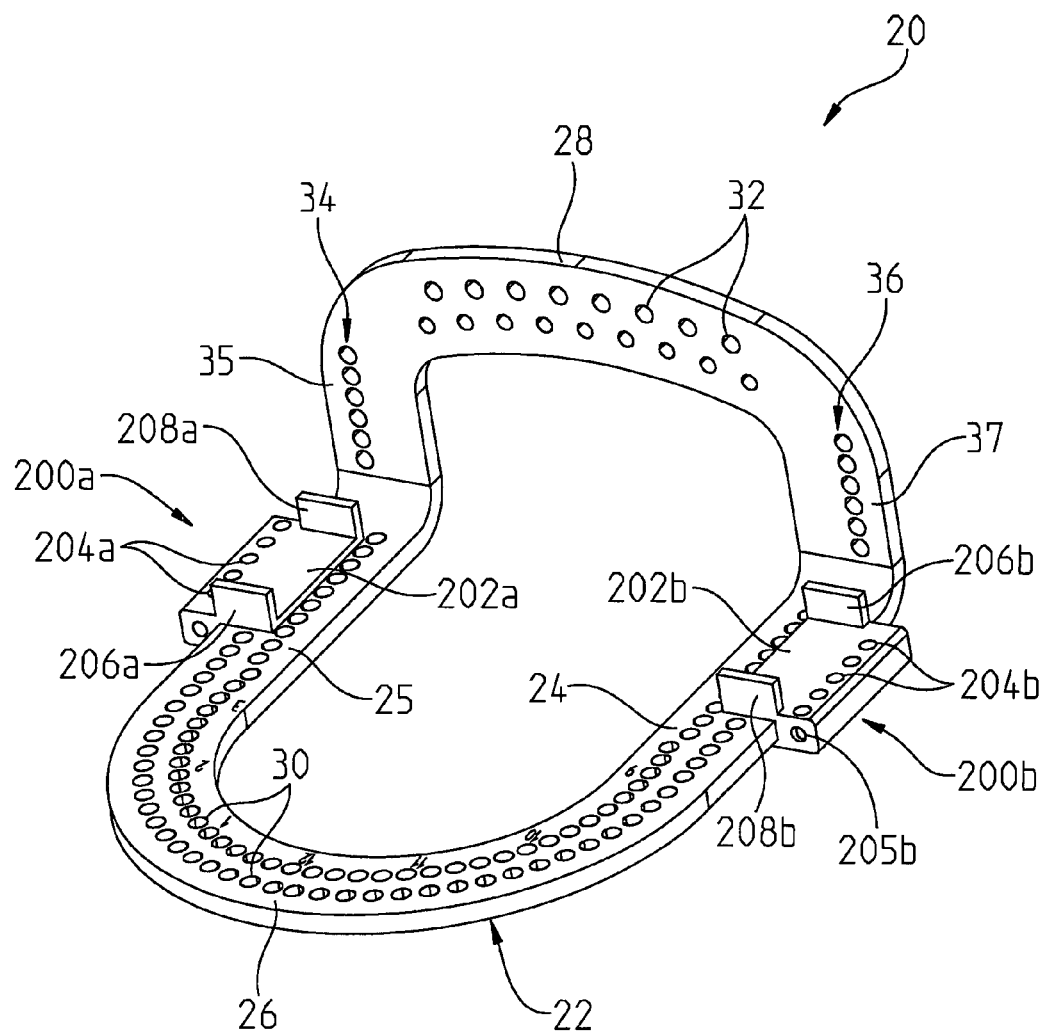
FIG. 13 is a top perspective view of a bone/joint frame in accordance with the principles of the subject invention having an embodiment of positionable compression rails.
Figure 14:
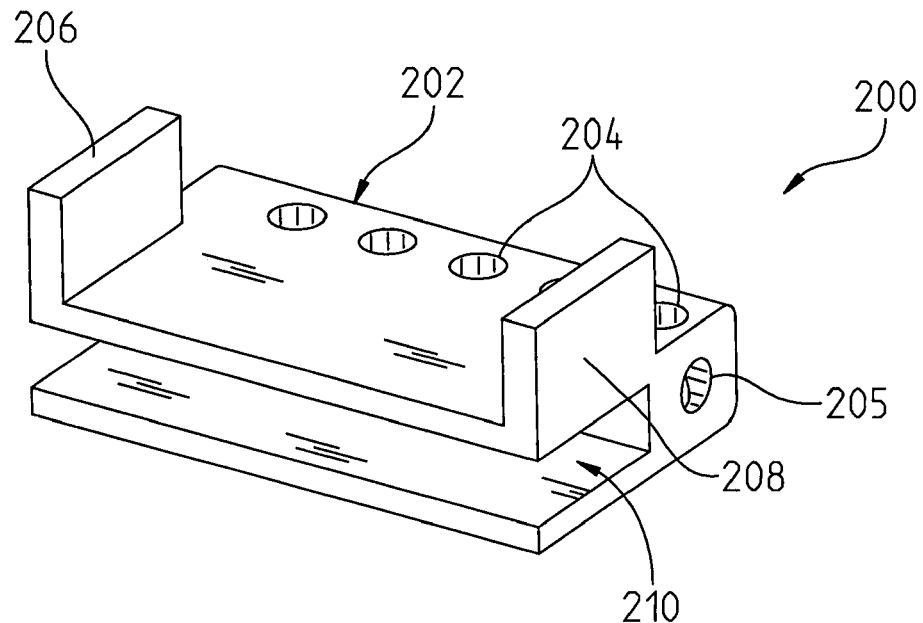
FIG. 14 is an enlarged perspective view of one of the compression rails of FIG. 13.

Referring now to FIG. 13, there is depicted the frame component 20 having first and second compression bars, rails, member, components or the like generally designated 200a and 200b. The compression rails 200a, 200b are preferably, but not necessarily, identical. The compression rails 200a and 200b are each configured to be releasably and/or adjustably received on the respective sides 25 and 24 of the frame, and particularly of the posterior portion thereof. As best seen in FIG. 14, wherein each rail 200a and 200b is represented by the compression rail 200.

In FIG. 14, the compression rail 200 is defined by a body 202 having a plurality of fixation bores 204 configured to receive wire fixation posts and/or members and a side bore 205. The body 202 defines a slot or channel 210 that is dimensioned to fit around the frame. In this manner the rail 200 is slidably adjustable on the frame. First and second transverse walls 206 and 208 extend from the body 202 and provide a guide for any fixation wires.

Figure 15:
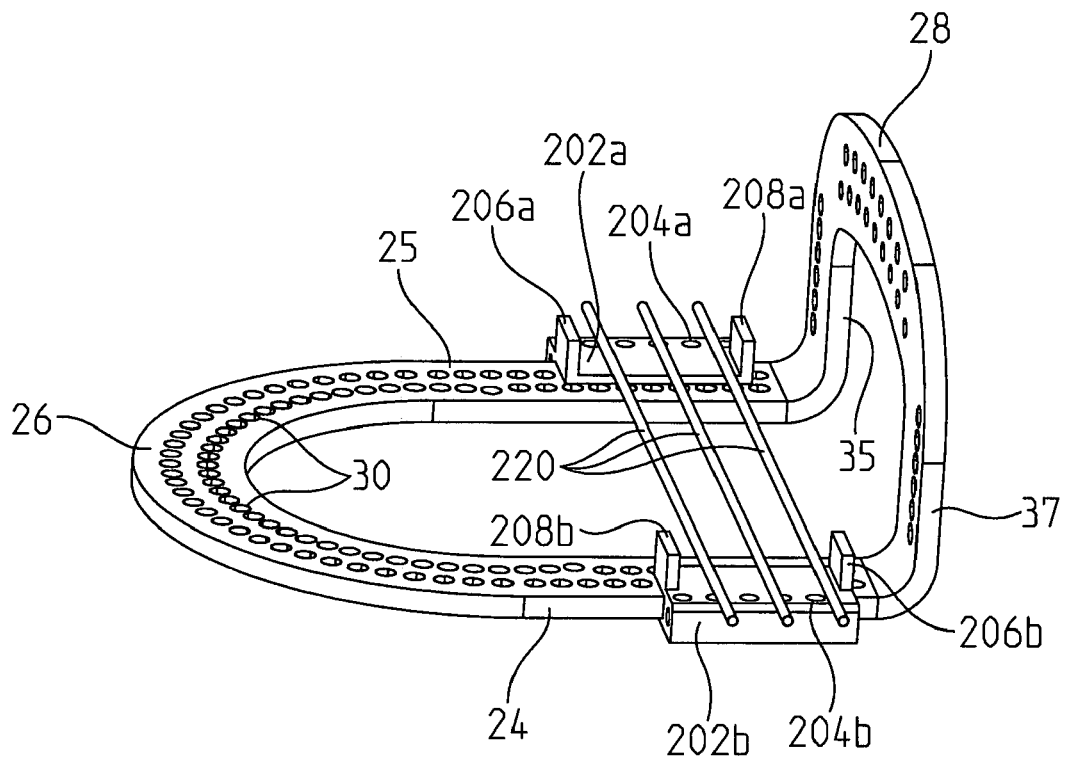
FIG. 15 is a side perspective view of the fixation frame construct of FIG. 13 with medial/lateral fixation wires superimposed thereon.

As seen in FIG. 15, various fixation wires 220 are provided in the medial/lateral direction from one compression rail 202a to the other compression rail 202b (although not shown fixed or attached thereto for clarity). These medial/lateral fixation wires can create anterior/posterior compression on the bone (e.g. foot/ankle). Placement of the compression rails may be staggered (i.e. not in the same position on each side of the frame).

Figure 16:
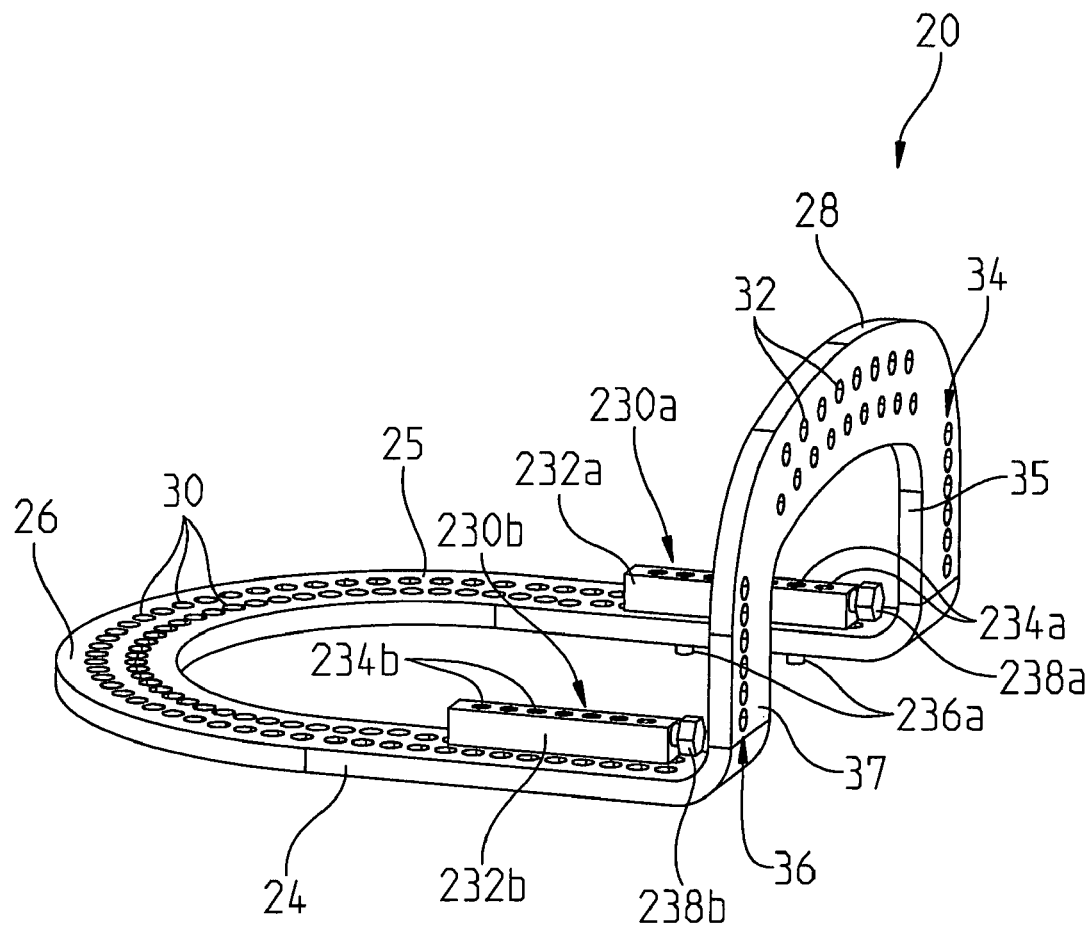
FIG. 16 is rear, side perspective view of a bone/joint frame in accordance with the principles of the subject invention having an alternative embodiment of positionable compression rails.
Figure 17:
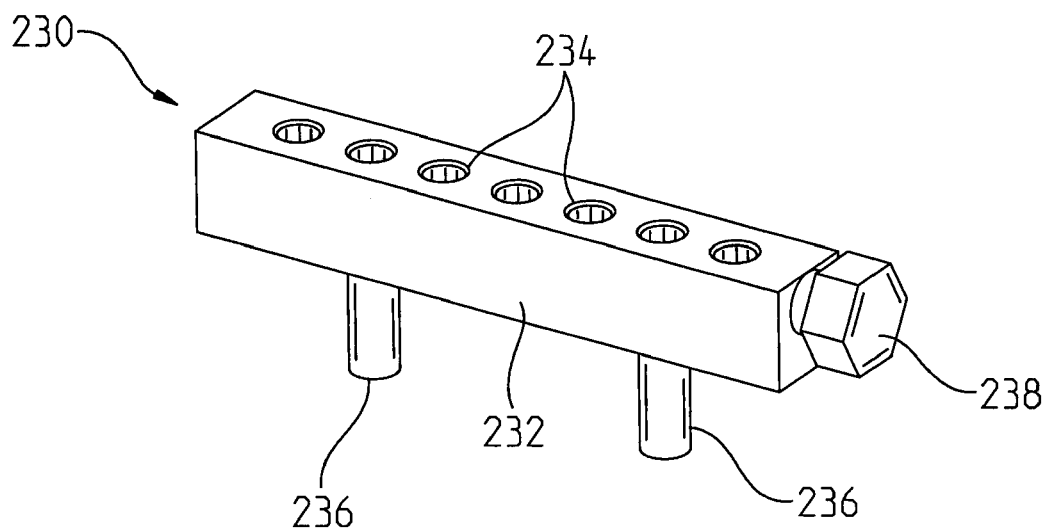
FIG. 17 is an enlarged perspective view of one of the compression rails of FIG. 16.

Referring now to FIG. 16, there is depicted the frame component 20 having first and second compression bars, rails, member, components or the like generally designated 230a and 230b. The compression rails 230a, 230b are preferably, but not necessarily, identical. The compression rails 230a and 230b are each configured to be releasably and/or adjustably received on the respect to sides 25 and 24 of the frame, and particularly of the posterior portion thereof. As best seen in FIG. 17, wherein each rail 230a and 230b is represented by the compression rail 230.

In FIG. 17, the compression rail 230 is defined by a body 232 having a plurality of fixation bores 234 configured to receive wire fixation posts and/or members and a side post 238. The body 232 has one or more mounting pegs 236 that are dimensioned to fit into the fixation bores of the frame. In this manner the compression rail 230 may be removably positioned almost anywhere along the frame.

Figure 18:
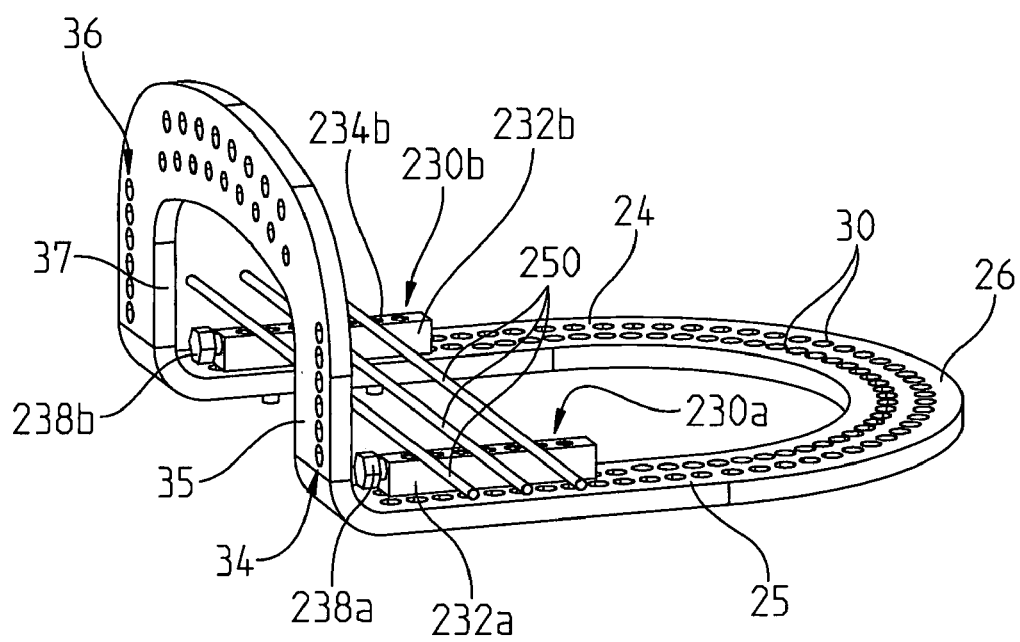
FIG. 18 is a side perspective view of the fixation frame construct of FIG. 16 with medial/lateral fixation wires superimposed thereon.

As seen in FIG. 18, various fixation wires, rods or the like 250 are provided in the medial/lateral direction from one compression rail 232a to the other compression rail 232b (although not shown fixed or attached thereto for clarity). These medial/lateral fixation wires can create anterior/posterior compression on the bone (e.g. foot/ankle). Placement of the compression rails may be staggered (i.e. not in the same position on each side of the frame).

Figure 19:
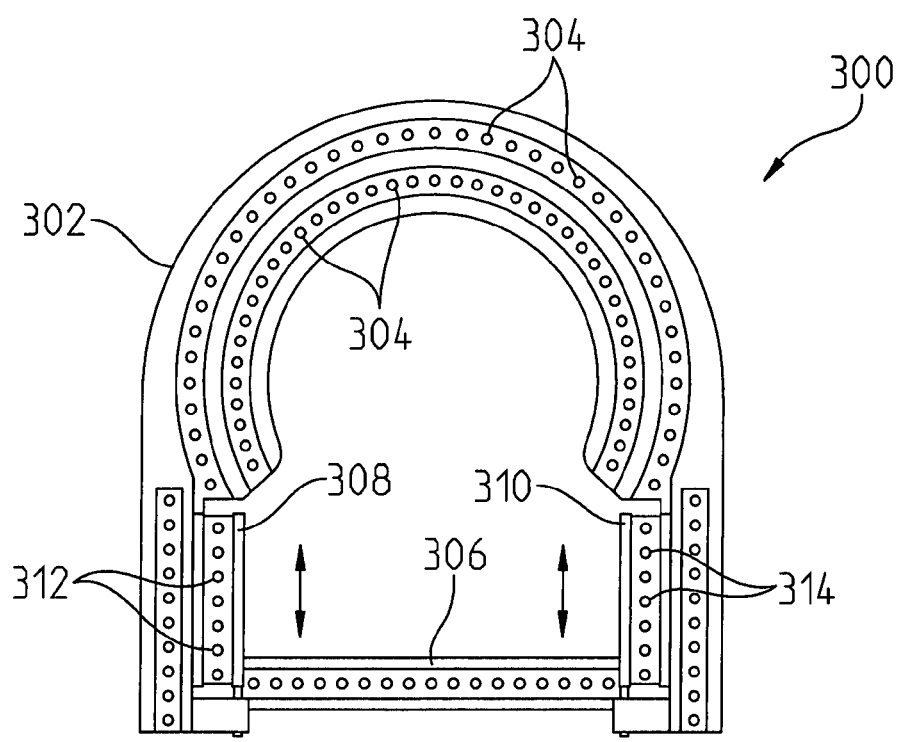
FIG. 19 is a top plan view of an exemplary alternative embodiment of an external bone/joint frame having an exemplary alternative embodiment of compression rails in accordance with an aspect of the principles of the subject invention.

In FIG. 19, there is depicted a bottom view of an alternative embodiment of an external ankle/foot fixation device generally designated 300. The fixation device 300 includes a frame 302 having a plurality of frame holes 304. A cross bar 306 extends across the frame 302. In accordance with an aspect of this embodiment, the fixation device 300 includes first and second compression rails 308 and 310. The compression rails 308, 310 each have a respective set of holes 312, 314. The holes 312, 314 allow the receipt of fixation posts/members for receiving fixation wires. As represented by the arrows, the compression rails 308, 310 limitedly move in an anterior/posterior direction. Other manners of providing controlled compression may be utilized. Various combinations of the above compression rails may be provided.

As seen in FIGS. 1 and 7, the frame 20 includes numbers or calibration markings as indicated above. These marking may be calibrated and/or used with respect to other fixation components not shown herein. The markings match the markings of the other fixation components for alignment of the foot frame to threaded rods. For example, rings with threaded rods may be used in addition to the present foot frame. These components have the calibration markings that are then compatible with the calibration markings of the present fixation device.

In another form, the markings may correspond to holes in other, non-marked components. For instance, another component may have a plurality of holes. Hole number of the other component would correspond to the number marking on the frame. Thus, if a fixation device was retained in a hole counted to be "12", the fixation wire attached thereto would correspond to the marking "12" on the frame, to which the other end of the fixation wire would be attached.

The frame or frame component in each case keeps the fixation wires straight (or relatively straight) with relation to the various clamping surfaces thereof. Further, the curvature of the frame is such as to preferably follow the shape of the bone/joint or placement area. Typically, the frame (posterior portion) is curved or arcuate and thus has a radius or radius of curvature particularly between the horizontal and vertical planes. This radius is preferably formed as a stress reduction radius. As such, the radius should be between 0.06 inches and 1.5 inches.

Moreover, the material from which the frame is fabricated should have little to no flexibility. This will address any springback and/or tensioning of the fixation wires situated thereon or thereby. Therefore, the frame is designed with A/P forces that tend to close the frame in mind. Particularly, the frame should be stiff enough to that under tension it will flex less than 0.5 mm in the transverse plane and less than 2.0 mm in the coronal plane.

What is claimed is:

1. An external bone/joint fixation device comprising:
   a frame component having a posterior portion and an anterior portion disposed transverse to said posterior portion, said frame component including a plurality of first fixation bores defined in said posterior portion;
   a cross bar assembly attachable to said anterior portion of said frame component, said cross bar assembly including a cross bar component fixable at any one of a plurality of positions in relation to said anterior portion, said cross bar component having a plurality of second fixation bores;
   a posterior angulation assembly attachable to said posterior portion of said frame component at any one of a plurality of positions in relation to said posterior portion; and
   a fixation wire extending from said posterior angulation assembly to said cross bar component,
   wherein said posterior portion includes (i) a first side frame segment, (ii) a second side frame segment spaced apart from said first side frame segment to define a first gap therebetween, and (iii) a first connector portion extending from said first side frame segment to said second side frame segment,
   wherein said anterior portion includes (i) a first leg, (ii) a second leg spaced apart from said first leg to define a second gap therebetween, and (iii) a second connector portion extending from said first leg to said second leg, said first side frame segment of said posterior portion is connected to said first leg of said anterior portion, said second side frame segment of said posterior portion is connected to said second leg of said anterior portion, and said fixation wire extends (i) over said first gap, and (ii) through said second gap.

2. The external bone/joint fixation device of claim 1, wherein said cross bar component is rotatable about a longitudinal axis of said cross bar component.

3. The external bone/joint fixation device of claim 1, wherein said cross bar assembly further includes first and second cross bar holders each configured for attachment to said anterior portion of said frame component and for receipt of an end of said cross bar.

4. The external bone/joint fixation device of claim 3, wherein each cross bar holder is configured to clamp against an end of the cross bar component when the cross bar holder is mounted to said anterior portion of said frame component.

5. The external bone/joint fixation device of claim 1, wherein said anterior portion extends above a first plane defined by said posterior portion.

6. The external bone/joint fixation device of claim 1, wherein said posterior angulation component defines a wire retention bore configured to receive a fixator for receipt of a portion of the fixation wire.

7. The external bone/joint fixation device of claim 6, wherein said posterior angulation component further defines a fastener bore alignable with any one of said plurality of first fixation bores defined in said posterior portion of said frame component.

8. The external bone/joint fixation device of claim 7, further comprising a fastener extending through said fastener bore and a first of said plurality of first fixation bores defined in said posterior portion of said frame component.

9. The external bone/joint fixation device of claim 1, further comprising an elevator configured to extend about a bottom portion of said frame component and allowing access to a sole of the foot.

10. The external bone/joint fixation device of claim 9, wherein said elevator is adapted to evenly distribute pressure applied thereto.

11. The external bone/joint fixation device of claim 9, wherein said elevator is arcuate shaped.

12. The external bone/joint fixation device of claim 1, wherein:
said frame component forms a continuous loop,
said posterior portion defines a first part of said continuous loop, and
said anterior portion defines a second part of said continuous loop.

13. The external bone/joint fixation device of claim 1, further comprising calibration markings disposed on said posterior portion.

14. The external bone/joint fixation device of claim 1, wherein said frame is fabricated from at least one of a composite material, a polymer, a metal alloy and a shape memory material.

15. The external bone/joint fixation device of claim 1, wherein said frame is fabricated from a radiolucent material.

16. A fixation device, comprising:
a frame having (i) a posterior portion defining a first plane, and (ii) an anterior portion defining a second plane which is non-coplanar in relation to said first plane;
a cross bar assembly coupled to said anterior portion of said frame;
a posterior angulation assembly coupled to said posterior portion of said frame; and
a fixation wire extending from said posterior angulation assembly to said cross bar assembly,
wherein said posterior portion includes (i) a first side frame segment, (ii) a second side frame segment spaced apart from said first side frame segment to define a first gap therebetween, and (iii) a first connector portion extending from said first side frame segment to said second side frame segment,
wherein said anterior portion includes (i) a first leg, (ii) a second leg spaced apart from said first leg to define a second gap therebetween, and (iii) a second connector portion extending from said first leg to said second leg,
said first side frame segment of said posterior portion is connected to said first leg of said anterior portion,
said second side frame segment of said posterior portion is connected to said second leg of said anterior portion, and
said fixation wire extends (i) over said first gap, and (ii) through said second gap.

17. The fixation device of claim 16, wherein:
said cross bar assembly includes a first end portion and a second end portion,
said first end portion is attached to said first leg of said anterior portion,
said second end portion is attached to said second leg of said anterior portion,
said cross bar assembly includes a cross bar component, and
said cross bar component is fixable to said anterior portion of said frame at any one of a plurality of positions.

18. The fixation device of claim 17, wherein said cross bar component is rotatable between (i) a first position of said plurality of positions, and (ii) a second position of said plurality of positions.

19. The fixation device of claim 16, wherein:
said cross bar assembly includes a cross bar component,
said cross bar assembly further includes a first holder and a second holder,
said first holder is securable to said first leg of said anterior portion of said frame,
said second holder is securable to said second leg of said anterior portion of said frame,
said first holder is configured to clamp a first end of said cross bar component, and
said second holder is configured to clamp a second end of said cross bar component.

20. The fixation device of claim 16, wherein said posterior angulation component is configured to be coupled to said posterior portion of said frame at any one of a plurality of positions along said posterior portion.

21. The fixation device of claim 20, wherein:
said posterior portion of said frame defines a plurality of first bores,
said posterior angulation component defines a fastener bore, and
said fastener bore is alignable with any one of said plurality of first bores.

22. The fixation device of claim 21, further comprising a fastener extending through said fastener bore and a first of said plurality of first fixation bores defined in said posterior portion of said frame.

23. The fixation device of claim 21, wherein:
said posterior angulation component further defines a wire retention bore, and said wire retention bore is configured to receive a fixator component therein.

24. The fixation device of claim 16, wherein:
said frame forms a continuous loop,
said posterior portion of said frame defines a first part of said continuous loop, and
said anterior portion of said frame defines a second part of said continuous loop.

25. The fixation device of claim 16, wherein:
said first plane and said second plane define an angle Θ, and 70°≦Θ≦110°.

26. The fixation device of claim 16, wherein:
said first plane and said second plane define an angle Θ, and Θ is approximately equal to 90°.

27. A fixation device, comprising:
a frame having (i) a posterior portion defining a first plane, and (ii) an anterior portion defining a second plane which is non-coplanar in relation to said first plane;
a cross bar assembly coupled to said anterior portion of said frame;
a posterior angulation assembly coupled to said posterior portion of said frame; and
a fixation wire extending from said posterior angulation assembly to said cross bar assembly,
wherein said posterior portion includes (i) a first side frame segment, (ii) a second side frame segment spaced apart from said first side frame segment to define a first gap therebetween, and (iii) a first connector portion extending from said first side frame segment to said second side frame segment,
wherein said anterior portion includes (i) a first leg, (ii) a second leg spaced apart from said first leg to define a second gap therebetween, and (iii) a second connector portion extending from said first leg to said second leg,
wherein said first side frame segment of said posterior portion is connected to said first leg of said anterior portion,
wherein said second side frame segment of said posterior portion is connected to said second leg of said anterior portion,
wherein said cross bar assembly includes (i) a cross bar component, (ii) a first holder configured to clamp a first part of said cross bar component, and (iii) a second holder configured to clamp a second part of said cross bar component,
wherein said first holder is secured to said first leg of said anterior portion of said frame, and
wherein said second holder is secured to said second leg of said anterior portion of said frame.

28. The fixation device of claim 27, wherein said fixation wire extends (i) over said first gap, and (ii) through said second gap.

29. The fixation device of claim 28, wherein said fixation wire further extends through said first gap.

30. The fixation device of claim 27, wherein:
said cross bar component is configured to be fixed to said anterior portion of said frame at any one of a plurality of positions, and
said cross bar component is rotatable between (i) a first position of said plurality of positions, and (ii) a second position of said plurality of positions.

31. The fixation device of claim 27, wherein said posterior angulation component is configured to be coupled to said posterior portion of said frame at any one of a plurality of positions along said posterior portion.

32. The fixation device of claim 31, wherein:
said posterior portion of said frame defines a plurality of first bores,
said posterior angulation component defines a fastener bore, and
said fastener bore is alignable with any one of said plurality of first bores.

33. The fixation device of claim 32, further comprising a fastener extending through said fastener bore and a first of said plurality of first fixation bores defined in said posterior portion of said frame.

34. The fixation device of claim 32, wherein:
said posterior angulation component further defines a wire retention bore, and
said wire retention bore is configured to receive a fixator component therein.

35. The fixation device of claim 27, wherein:
said frame forms a continuous loop,
said posterior portion of said frame defines a first part of said continuous loop, and
said anterior portion of said frame defines a second part of said continuous loop.

36. The fixation device of claim 27, wherein:
said first plane and said second plane define an angle Θ, and 70°≦Θ≦110°.

37. The fixation device of claim 27, wherein:
said first plane and said second plane define an angle Θ, and Θ is approximately equal to 90°.

\* \* \* \* \*